United States Patent
Freitag

(10) Patent No.: US 7,569,717 B2
(45) Date of Patent: Aug. 4, 2009

(54) DIARYL ALKYLPHOSPHONATES AND METHOD FOR PREPARING SAME

(75) Inventor: Dieter Freitag, Chelmsford, MA (US)

(73) Assignee: FRX Polymers, LLC, Chelmsford, MA (US)

( * ) Notice: Subject to any disclaimer, the term of this patent is extended or adjusted under 35 U.S.C. 154(b) by 220 days.

(21) Appl. No.: 11/458,274

(22) Filed: Jul. 18, 2006

(65) Prior Publication Data
US 2007/0021626 A1 Jan. 25, 2007

Related U.S. Application Data

(60) Provisional application No. 60/700,581, filed on Jul. 19, 2005, provisional application No. 60/747,892, filed on May 22, 2006.

(51) Int. Cl.
*C07C 69/76* (2006.01)
(52) U.S. Cl. .................................................. 558/90
(58) Field of Classification Search ................... 558/90
See application file for complete search history.

(56) References Cited

U.S. PATENT DOCUMENTS

| | | | |
|---|---|---|---|
| 2,534,242 A | 12/1950 | Cusic | |
| 2,682,522 A | 6/1954 | Coover, Jr. et al. | |
| 2,716,101 A | 8/1955 | Coover, Jr. et al. | |
| 3,153,008 A | 10/1964 | Fox | |
| 3,271,329 A | 9/1966 | Coover, Jr. et al. | |
| 3,326,852 A | 6/1967 | Thomas | |
| 3,442,854 A | 5/1969 | Curtius et al. | |
| 3,932,351 A | 1/1976 | King | |
| 3,932,566 A | 1/1976 | Reader | |
| 3,952,072 A | 4/1976 | Yonemitsu et al. | |
| 4,033,927 A | 7/1977 | Borman | |
| 4,048,106 A | 9/1977 | Hermans | |
| 4,064,107 A | 12/1977 | Stackman et al. | |
| 4,078,016 A | 3/1978 | Kramer | |
| 4,093,582 A | 6/1978 | Mark et al. | |
| 4,152,373 A | 5/1979 | Honig et al. | |
| 4,254,177 A | 3/1981 | Fulmer | |
| 4,332,921 A | 6/1982 | Schmidt et al. | |
| 4,377,537 A | 3/1983 | Block et al. | |
| 4,408,033 A | 10/1983 | Hefner, Jr. | |
| 4,474,937 A | 10/1984 | Bales | |
| 4,594,404 A | 6/1986 | Kawakami et al. | |
| 4,736,052 A | 4/1988 | Nunan et al. | |
| 5,003,029 A | 3/1991 | Ueda et al. | |
| 5,034,056 A | 7/1991 | VonBonin | |
| 5,039,775 A | 8/1991 | Oyaizu | |
| 5,086,153 A | 2/1992 | Oyaizu | |
| 5,216,113 A | 6/1993 | Schulz-Schlitte et al. | |
| 5,254,709 A | 10/1993 | Hunter | |
| 5,319,058 A | 6/1994 | Hattori et al. | |
| 5,334,692 A | 8/1994 | Hess et al. | |
| 5,525,681 A | 6/1996 | Barron et al. | |
| 5,639,800 A | 6/1997 | VonBonin et al. | |
| 5,719,200 A | 2/1998 | Staendeke et al. | |
| 5,919,844 A | 7/1999 | Shimizu et al. | |
| 6,066,700 A | 5/2000 | Konig et al. | |
| 6,291,630 B1 | 9/2001 | Konig et al. | |
| 6,861,499 B2 | 3/2005 | Vinciguerra | |
| 2004/0167284 A1 | 8/2004 | Vinciguerra et al. | |
| 2005/0020800 A1 | 1/2005 | Levchik et al. | |
| 2005/0222370 A1 | 10/2005 | Freitag et al. | |
| 2006/0020104 A1 | 1/2006 | Freitag | |
| 2008/0045673 A1* | 2/2008 | Piotrowski et al. | .......... 525/538 |

FOREIGN PATENT DOCUMENTS

| | | |
|---|---|---|
| EP | 0077493 B1 | 3/1987 |
| GB | 2043083 | 1/1980 |
| WO | WO 03/029258 A1 | 4/2003 |
| WO | WO 2004/076536 | 9/2004 |
| WO | WO 2004/076537 | 9/2004 |

OTHER PUBLICATIONS

Schmidt et al., Aromatische Polyphosphonate: Thermoplastische Polymere von extremer Brandwidrigeit, 1985, Die Angewandte Makromolekulare Chemie, 132(2165):1-18.
Billmeyer, Textbook of Polymer Science, 2$^{nd}$ ed., Wiley Interscience, New York, 1971, pp. 45-52.
Legrand et al., eds., Handbook of Polycarbonates, Marcel Dekker, Inc., New York, 2000 (TOC).
Levchik et al., Overview of Recent Developments in the Flame Retardancy of Polycarbonates, Polymer International, 54(7):981-998, 2005.
Cotter et al., Engineering Plastics: A Handbook of Polyarylethers, Science Publ. S.A., Switzerland 1995 (TOC).
Groggins, Unit Processes in Organic Synthesis, 4$^{th}$ ed., McGraw Hill Book Co., 1952, pp. 616-620.
Morgan, Condensation Polymers, Wiley Interscience, New York, 1965, pp. 217-223.

* cited by examiner

*Primary Examiner*—Rei-tsang Shiao
(74) *Attorney, Agent, or Firm*—Pepper Hamilton LLP

(57) ABSTRACT

A method of making optionally substituted diaryl alkylphosphonates from an optionally substituted arylol, an optionally substituted alkanol, and a phosphorous trihalide is described.

25 Claims, No Drawings ial Application No. 60/700,581 entitled "Method for Preparing Diaromatic Alkylphosphonates" filed Jul. 19, 2005, and U.S. Provisional Application No. 60/747,892 entitled "Method for Preparing Diaromatic Alkylphosphonates" filed May 22, 2006, the contents of which are incorporated herein by reference in their entirety.

BACKGROUND

Various methods for the synthesis of diaromatic alkylphosphonates are known. Methods for making diaromatic alkylphosphonates are described in U.S. Pat. Nos. 4,152,373 and 4,377,537, for example. In U.S. Pat. No. 4,152,373, diaromatic alkylphosphonates are prepared by the reaction of a triaromaticphosphite specifically triphenylphosphite and methanol in the presence of a catalytic amount of methyl iodide. The reaction temperatures are higher than the boiling point of methanol (~65° C.), and consequently require a relatively slow addition of methanol in order to keep it from boiling out of the reactor. In this reaction, phenol is a by-product that is distilled from the product in a separate step.

U.S. Pat. No. 4,377,537 described a method of synthesiszing diaromatic methylphosphonates by the reaction of a triarylphosphite (specifically triphenylphosphite) and trialkylphosphite (specifically trimethylphosphite) in the presence of a catalytic amount of methyl iodide. The reaction typically involved heating the components to a final temperature of about 230° C. for up to 1 hour. Exothermic reactions for this process occur in two temperature regions, the first around 100° C., and the second near 210° C. Due to the exothermic (even explosive) nature of these reactions when used in a batch process the reaction scheme described in U.S. Pat. No. 4,377,537 is limited to small scale production of diaromatic alkylphosphonates.

Although some diaromatic alkylphosphonates (e.g. diphenyl methylphosphonate (Registry number 7526-26-3) are commercially available, they are relatively expensive.

SUMMARY

Various embodiments of the present invention may include a composition comprising a phosphorous trihalide, an optionally substituted alkanol, and an optionally substituted arylol. Various other embodiments of the invention may include a composition comprising the product from reacting phosphorous trihalide and optionally substituted arylol, and optionally substituted alkanol. The compositions of embodiments of the invention may be useful for making optionally substituted diaryl alkylphosphonate. In some embodiments, the phosphorous trihalide may be phosphorous trichloride, the optionally substituted alkanol may be methanol, and the optionally substituted arylol may be phenol. In other embodiments, the composition further comprise an alkylating catalyst that may be, but not limited to, alkyl halides, sufonic acid esters, sulfuric acid esters, sulftones, trifluoromethane sulfuric acid, perfluorobutane sulfuric acid, perfluorooctane sulfuric acid and combinations thereof, and in certain embodiments, the alkylating catalyst may be methyl iodide. In some embodiments, the optionally substituted arylol in the mixture may be from about 1 to about 4 molar equivalents of the phosphorous trihalide and the optionally substituted alkanol may be from about 1 about 3 molar equivalents of the phosphorous trihalide.

Various other embodiments of the present invention provide for a composition that includes a phosphorous trihalide, an optionally substituted alkanol, an optionally substituted arylol and a catalyst, and still other embodiments provide for compositions that may include the product from reacting phosphorous trihalide and optionally substituted arylol and optionally substituted alkanol. The compositions of embodiments of the invention may be useful for making optionally substituted diaryl alkylphosphonate. In some embodiments, the phosphorous trihalide may be phosphorous trichloride, the optionally substituted alkanol may be methanol, the optionally substituted arylol may be phenol and the alkylating catalyst may be, but not limited to, alkyl halides, sufonic acid esters, sulfuric acid esters, sulftones, trifluoromethane sulfuric acid, perfluorobutane sulfuric acid, prefluorooctane sulfuric acid and combinations thereof, and in certain embodiments, the alkylating catalyst may be methyl iodide. In some embodiments, the optionally substituted arylol in the mixture may be from about 1 to about 4 molar equivalents of the phosphorous trihalide, the optionally substituted alkanol may be from about 1 about 3 molar equivalents of the phosphorous trihalide, and the catalyst may be from 0 to about 10% by weight of the phosphorous trihalide.

Still other embodiments of the present invention provide for a composition including a phosphorous trihalide, and optionally substituted arylol wherein about 1 to about 4 molar equivalents of the optionally substituted arylol may be added per mole of phosphorous trihalide, and optionally substituted alkanol wherein about 1 to about 3 molar equivalents of the optionally substituted alkanol are added per mole of phosphorous trihalide. In some embodiments, the phosphorous trihalide may be phosphorous trichloride, the optionally substituted alkanol may be methanol and the optionally substituted arylol may be phenol. In other embodiments, the composition further comprises an alkylating catalyst such as but not limited to alkyl halides, sufonic acid esters, sulfuric acid esters, sulftones, trifluoromethane sulfuric acid, perfluorobutane sulfuric acid, prefluorooctane sulfuric acid and combinations thereof, and in certain embodiments, the alkylating catalyst may be methyl iodide.

Further embodiments of the present invention include a method for making optionally substituted diaryl alkylphosphonate, such as, for example, diphenylmethylphosphonate, comprising combining phosphorous trihalide, optionally substituted arylol and optionally substituted alkanol to form a mixture and heating the mixture. In still further embodiments, the method of the invention comprises reacting phosphorous trihalide and optionally substituted arylol, adding an optionally substituted alkanol to form a mixture and heating the mixture. In some embodiments, the phosphorous trihalide may be phosphorous trichloride, the optionally substituted alkanol may be methanol, and the optionally substituted arylol may be phenol. In some embodiments of the invention, volatile products and by-products of the reaction are removed from the reaction mixture in a further step in the method. In other embodiments, the method further includes the step of adding an alkylating catalyst such as but not limited to alkyl halides, sufonic acid esters, sulfuric acid esters, sulftones, trifluoromethane sulfuric acid, perfluorobutane sulfuric acid, prefluorooctane sulfuric acid and combinations thereof, and in certain embodiments, the alkylating catalyst may be methyl iodide. The catalyst may be added at from 0 to about 10% by weight of the phosphorous trihalide. In some embodiments, the optionally substituted arylol in the mixture may be from about 1 to about 4 molar equivalents of the phosphorous trihalide and the optionally substituted alkanol may be from about 1 about 3 molar equivalents of the phosphorous trihalide. The mixture may be heated from about 23° C. to about 260° C.

In certain embodiments of the method of the present invention, no outside catalyst is added to the mixture.

In certain other embodiments of the method of the present invention, substantially no triaryl phosphite may be found in the final reaction product, and in certain other embodiments, about 30 mol % or more excess of optionally substituted alkanol relative to the phosphorous trihalide may be added to the mixture resulting in a final reaction product having substantially no triaryl phosphite. In such embodiments, triaryl phosphite evolved during the course of the reaction may be consumed during the reaction.

In other embodiments of the method of the present invention, the method may further includes the step of adding an alkylating catalyst such as but not limited to alkyl halides, sufonic acid esters, sulfuric acid esters, sulftones, trifluoromethane sulfuric acid, perfluorobutane sulfuric acid, prefluorooctane sulfuric acid and combinations thereof, and in certain embodiments, the alkylating catalyst may be methyl iodide. The catalyst may be added at from 0 to about 10% by weight of the phosphorous trihalide.

In still other embodiments of the method of the present invention may include the steps of combining phosphorous trihalide and optionally substituted arylol to form a mixture, heating the mixture or reacting phosphorous trihalide and optionally substituted arylol, and adding the optionally substituted alkanol from below the surface of the mixture. In some embodiments, the alkanol may be pumped into the mixture using a pump. The reaction efficiency, conversion time and yield of the method may be improved by pumping the optionally substituted alkanol into the mixture when compared to a similar reaction to which the optionally substituted alkanol is added by a drop wise overhead method. In some embodiments, the phosphorous trihalide may be phosphorous trichloride, the optionally substituted alkanol may be methanol, and the optionally substituted arylol may be phenol. In some embodiments of the invention, volatile products and by-products of the reaction are removed from the reaction mixture in a further step in the method. In other embodiments, the method further includes the step of adding an alkylating catalyst such as but not limited to alkyl halides, sufonic acid esters, sulfuric acid esters, sulftones, trifluoromethane sulfuric acid, perfluorobutane sulfuric acid, prefluorooctane sulfuric acid and combinations thereof, and in certain embodiments, the alkylating catalyst may be methyl iodide. In embodiments where a catalyst is added, the catalyst may be added with the alkanol from below. The catalyst may be added at from 0 to about 10% by weight of the phosphorous trihalide. In some embodiments, the optionally substituted arylol in the mixture may be from about 1 to about 4 molar equivalents of the phosphorous trihalide and the optionally substituted alkanol may be from about 1 about 3 molar equivalents of the phosphorous trihalide. The mixture may be heated from about 23° C. to about 260° C.

In still other embodiments of the method of the present invention, the method includes combining phosphorous trihalide, optionally substituted arylol, optionally substituted alkanol, and a catalyst to form a mixture, and heating the mixture. In some embodiments, the catalyst is an alkylating catalyst such as but not limited to alkyl halides, sufonic acid esters, sulfuric acid esters, sulftones, trifluoromethane sulfuric acid, perfluorobutane sulfuric acid, prefluorooctane sulfuric acid and combinations thereof, and in certain embodiments, the alkylating catalyst may be methyl iodide.

In yet other embodiments of the method of the present invention, the method includes reacting phosphorous trihalide and optionally substituted arylol, adding optionally substituted alkanol to form a mixture, and heating the mixture to a temperature at which the exothermic reaction associated with the formation of the optionally substituted diaryl alkyphosphonate may be exceeded. In some embodiments of the invention, volatile products and by-products of the reaction are removed from the reaction mixture in a further step in the method. In other embodiments, the method further includes the step of adding an alkylating catalyst such as but not limited to alkyl halides, sufonic acid esters, sulfuric acid esters, sulftones, trifluoromethane sulfuric acid, perfluorobutane sulfuric acid, prefluorooctane sulfuric acid and combinations thereof, and in certain embodiments, the alkylating catalyst may be methyl iodide. In some embodiments where a catalyst is added, the catalyst may be added with the alkanol from below. The catalyst may be added at from 0 to about 10% by weight of the phosphorous trihalide.

The methods of embodiments of the present invention may form a commercially relevant yield of the product, and the product may be an optionally substituted diaryl alkylphosphonate. A commercially relevant yield may be a yield of greater than about 30% optionally substituted diaryl alkylphosphonate in some embodiments of the invention and greater than about 50% or greater than about 60% in other embodiments. In certain embodiments of the invention, a commercially relevant yield is greater than about 80% or, in some, greater than about 90%.

The present invention further provides for embodiments that include an optionally substituted diaryl alkylphosphonate made by the process including combining phosphorous trihalide, optionally substituted alrylol, and optionally substituted alkanol to form a mixture, and heating the mixture or reacting phosphorous trihalide and optionally substituted arylol, adding optionally substituted alkanol to form a mixture and heating the mixture. In some embodiments, the phosphorous trihalide may be phosphorous trichloride, the optionally substituted alkanol may be methanol, and the optionally substituted arylol may be phenol. In some embodiments of the invention, volatile products and by-products of the reaction are removed from the reaction mixture in a further step in the method. In other embodiments, the process may further include the step of adding an alkylating catalyst such as but not limited to alkyl halides, sufonic acid esters, sulfuric acid esters, sulftones, trifluoromethane sulfuric acid, perfluorobutane sulfuric acid, prefluorooctane sulfuric acid and combinations thereof, and in certain embodiments, the alkylating catalyst may be methyl iodide. The catalyst may be added at from 0 to about 10% by weight of the phosphorous trihalide. In some embodiments, the optionally substituted arylol in the mixture may be from about 1 to about 4 molar equivalents of the phosphorous trihalide and the optionally substituted alkanol may be from about 1 about 3 molar equivalents of the phosphorous trihalide. The mixture may be heated from about 23° C. to about 260° C. In other embodiments, the alkanol may be added from below.

The optionally substituted diaryl alkylphosphonate prepared using methods of embodiments of the present invention may be made in a commercially relevant yield. A commercially relevant yield may be a yield of greater than about 30% optionally substituted diaryl alkylphosphonate in some embodiments of the invention and greater than about 50% or greater than about 60% in other embodiments. In certain embodiments of the invention, a commercially relevant yield is greater than about 80% or, in some, greater than about 90%.

DETAILED DESCRIPTION

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a", "an", and "the" include plural reference unless the context clearly dictates otherwise. Unless defined otherwise, all technical and scientific terms and herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

The term "alkyl" or "alkyl group" refers to a branched or unbranched hydrocarbon or group of 1 to 20 carbon atoms, such as but not limited to methyl, ethyl, n-propyl, isopropyl, n-butyl, isobutyl, t-butyl, octyl, decyl, tetradecyl, hexadecyl, eicosyl, tetracosyl and the like. "Cycloalkyl" or "cycloalkyl groups" are branched or unbranched hydrocarbons in which all or some of the carbons are arranged in a ring such as but not limited to cyclopentyl, cyclohexyl, methylcyclohexyl and the like. The term "lower alkyl" includes an alkyl group of 1 to 10 carbon atoms.

The term "aryl" or "aryl group" refers to monovalent aromatic hydrocarbon radicals or groups consisting of one or more fused rings in which at least one ring is aromatic in nature. Aryls may include but are not limited to phenyl, napthyl, biphenyl ring systems and the like. The aryl group may be unsubstituted or substituted with a variety of substituents including but not limited to alkyl, alkenyl, halide, benzylic, alkyl or aromatic ether, nitro, cyano and the like and combinations thereof.

"Substituent" refers to a molecular group that replaces a hydrogen in a compound and may include but are not limited to trifluoromethyl, nitro, cyano, $C_1$-$C_{20}$ alkyl, aromatic or aryl, halide (F, Cl, Br, I), $C_1$-$C_{20}$ alkyl ether, benzyl halide, benzyl ether, aromatic or aryl ether, hydroxy, alkoxy, amino, alkylamino (—NHR'), dialkylamino (—NR'R") or other groups which do not interfere with the formation of the diaryl alkylphosphonate.

As defined herein, an "arylol" or an "arylol group" is an aryl group with a hydroxyl, OH, group substituent on the aryl ring. One non-limiting examples of an arylol are phenol, naphthalene and the like. A wide variety of arylols may be used in the embodiments of the invention and are commercially available.

The term "alkanol" or "alkanol group" refers to a compound comprising an alkyl of 1 to 20 carbon atoms or more having at least one hydroxyl group substituent. Examples of alkanols include but are not limited to methanol, ethanol, 1- and 2-propanol, 1,1-dimethylethanol, hexanol, octanol and the like. Alkanol groups may be optionally substituted with substituents as described above.

The term "alkanol" or "alkanol group" refers to a compound comprising an alkene 2 to 20 carbon atoms or more having at least one hydroxyl group substituent. The hydroxyl may be arranged in either isomeric configuration (cis or trans). Alkenols may be further substituted with one or more substituents as described above and may be used in place of alkanols in some embodiments of the invention. Alkenols are known to those skilled in the art and many are readily available commercially.

The term "commercially relevant" or "commercially relevant yield" may refer to the yield of a product that is sufficient for use commercially and, generally, may be greater than about 10% and up to about 100%.

One of the embodiments of the present invention provides a method for making optionally substituted diaryl alkylphosphonates, diaryl alkylphosphonates prepared using the method, and compositions related to the method. The method includes preparing a mixture having an optionally substituted arylol, a phosphorous trihalide and an optionally substituted alkanol. For example, in one embodiment of the invention, an optionally substituted arylol may be introduced into a flask and heated. A phosphorous trihalide may then be added over a period of time. The time may vary depending upon the amount of material to be produced. Additional heating steps of various temperatures may be performed to drive the reaction and aid in the removal of generated acids and excess arylol. An optionally substituted alkanol may be added over a second period of time and the reaction may be heated. The reaction may proceed without addition of a catalyst. Alternatively, a catalyst (e.g. an alkylating agent) may be added along with the alkanol or after addition of the alkanol. The temperature may then be increased. The reaction may continue until the reaction has gone to completion. The optionally substituted diaryl alkylphosphonate product of the reaction may then be analyzed by GC/MS. In certain embodiments, the method described above is used to make diphenylmethylphosphonate.

One embodiment of the present invention provides for a composition having an optionally substituted arylol, a phosphorous trihalide, and an optionally substituted alkanol that may be useful for making diaryl alkylphosphonates. In other embodiments, the composition may comprise the product from reacting phosphorous trihalide and optionally substituted arylol, and optionally substituted alkanol. In another embodiment, the composition comprises an optionally substituted arylol, a phosphorous trihalide, an optionally substituted alkanol, and a catalyst.

In another embodiment, an optionally substituted arylol, an optionally substituted alkanol, phosphorous trihalide or any combination of these are combined in a vessel to form a diaryl alkylphosphonate without an exogenous catalyst. While not wishing to be bound by theory, it is believed in this embodiment an in situ catalyst is formed by the reaction.

In one embodiment, the diaryl alkylphosphonates of the present invention may be prepared in a single reaction vessel providing, as part of the present invention, a method for a one-pot synthesis or diaryl alkylphosphonate.

The diaryl alkylphosphonates or optionally substituted diaryl alkylphosphonates encompassed by embodiments of the current invention may be of general formula (1):

(1)

where $R_1$ may be an aromatic or aryl group, or a substituted aryl group of formula (2):

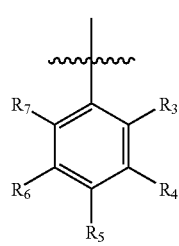

(2)

where $R_3$, $R_4$, $R_5$, $R_6$, and $R_7$ may independently be any substituent including but not limited to hydrogen, $C_1$-$C_{20}$ alkyl, aromatic or aryl group, trifluoromethyl, nitro, cyano, halide (F, Cl, Br, I), $C_1$-$C_{20}$ alkyl ether, benzyl halide, benzyl ether, aromatic or aryl ether, or optionally substituted versions of these, and $R_3$, $R_4$, $R_5$, $R_6$, and $R_7$ are essentially unaffected by the reaction. Phosphorus trihalides may be of general formula $PX_3$, or $X_aP(Oaryl)_b$, or other suitable phosphorous containing compounds. In some embodiments, X may be a halide such as F, Cl, Br or I; and a and b may be either 1 or 2 where a and b combined equals 3. In certain embodiments, the phosphorous trihalide may be phosphorous trichloride.

Optionally substituted arylol may be of general formula (3):

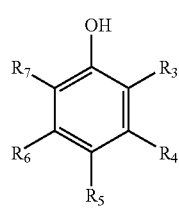

(3)

where $R_3$, $R_4$, $R_5$, $R_6$, and $R_7$ may independently be any substituent including but not limited to hydrogen, $C_1$-$C_{20}$ alkyl, aromatic or aryl group, trifluoromethyl, nitro, cyano, halide (F, Cl, Br, I), $C_1$-$C_{20}$ alkyl ether, benzyl halide, benzyl ether, aromatic or aryl ether, or optionally substituted versions of these, and $R_3$, $R_4$, $R_5$, $R_6$, and $R_7$ are essentially unaffected by the reaction. In certain embodiments of the present invention, an optionally substituted arylol may be phenol or naphthol or an optionally substituted phenol or naphthol derivative.

Various molar ratios of the reactants, the optionally substituted arylol and alkanol relative to the phosphorous trihalide, may be used. In embodiments of the invention, the molar ratio ranges from about 2 to about 4 molar equivalents for the optionally substituted arylol and from about 1 to about 3 molar equivalents for the alkanol and, in some embodiments, less than 2 molar equivalents. In some embodiments, the amount of catalyst may range from about 0 (i.e. no catalyst) to about 10% by weight of phosphorous trihalide, and in others, the catalyst ranges from about 0 to about 5% by weight of phosphorous trihalide, and in still others, the catalyst may range from about 0 to about 0.4% by weight of the phosphorous trihalide.

The method of the present invention is not limited by how the reactants are combined or their order of addition. For example, phosphorous trihalide may be added to an optionally substituted arylol followed by an optionally substituted alkanol. A catalyst may optionally be added thereto. Alternatively, several reactants can be combined in a single step. For example, a mixture of an optionally substituted arylol and an optionally substituted alkanol may be added to a phosphorous trihalide. A catalyst may, optionally, be introduced at any stage in the reaction or may be added in combination with one or more of the other reactants.

In some embodiments, one or more of the reactants and or catalysts may be added to the mixture via an addition funnel in an overhead method wherein the one or more reactants and/or catalysts are added onto the upper surface of the reaction mixture, and in others, one or more reactants and/or catalyst may be pumped into the reaction mixture thereby adding the constituent underneath the upper most surface of the reaction. Without wishing to be bound by theory, the addition of one or more reactants and/or catalysts to the reaction mixture thereby allowing the chemical reaction to have more time to occur before the alkanol turns to vapor. Using this approach, a constant stream of alkanol (and, optionally, a catalyst) may be provided under the surface of the reaction product of an optionally substituted arylol and phosphorous trihalide. Without wishing to be bound by theory, the resulting increased contact time may improve reaction efficiency, conversion time and product yield. It may also allow for an increased feed rate of alkanol, thereby reducing the reaction time compared to the dropwise overhead addition method.

No catalyst is necessary in the present invention. However, one or more catalysts, including, but not limited to, alkylating agents may be used. Other catalysts would be known to one skilled in the art. Catalysts may be added to the reaction mixture as an individual component, or in some embodiments of the present invention, the catalyst may be combined with one or more of the reactants prior to the addition of this combination to the reaction mixture.

In some embodiments, the catalyst may include, but are not limited to, alkyl chlorides, alkyl bromides and alkyl iodides in which the alkyl group may carry one or more of a variety of substituents. In other embodiments, methyl iodide is included in the catalyst. Other known alkylating catalysts that may be used in combination with the present invention include, but are not limited to, sulfonic acid esters, sulfuric acid esters, and sultones. Strong acids such as, but not limited to, trifluoromethane sulfonic acid, perfluorobutane sulfonic acid and perfluorooctane sulfonic acid may also serve as catalysts in this reaction. In embodiments where a catalyst is added below 100° C., an exotherm may be observed during heating, an in certain embodiments, the exotherm may be minor. In embodiments where the catalyst is added above 200° C. no exotherm may be observed.

The temperature of the reaction may range from about 20° C. to about 260° C. In some embodiments, the temperature at which the alkanol is added is about 150° C., followed by cooling, adding the catalyst and heating again to about 250° C.

In a certain embodiment, methanol (along with the catalyst) may be added to the reaction product of phenol and phosphorous trichloride ($PCl_3$) which may be heated to temperatures of from about 200° C. to 250° C.

Without wishing to be bound by theory in some embodiments of the present invention, the synthesis of diaryl alkylphosphonate may occur in two steps as illustrated in scheme (1):

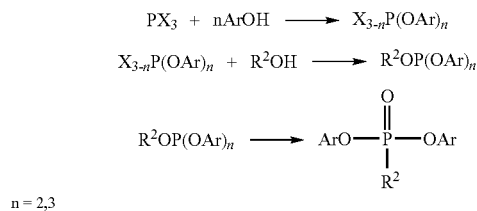

n = 2,3

In a first step, an optionally substituted arylol may react with a phosphorous trihalide to form a triarylphosphite. The triarylphosphite may then react with an optionally substituted alkanol to form an alkyl-diaryl phosphite and an arylol. The alkyl-diaryl phosphite may then be converted to diaryl alkylphosphonate. This may occur in the absence of a catalyst. In some embodiments, a catalyst may be added to facilitate the conversion of alkyl-diaryl phosphite to diaryl alkylphosphonate. In an alternative embodiment, phosphorous trihalide may react with an arylol to form diaryl halophosphite. Diaryl halophosphite may then be exposed to an alkanol (e.g. methanol) to form diaryl alkylphosphite, which may then be converted to diaryl alkylphosphonate.

Advantageously, reactants such as triaryl phosphites and trialkyl phosphites may not be required to form the diaryl alkylphosphonates, so there may be no need to isolate or purify intermediates such as triaryl phosphite. Additionally, by-products such as dialkyl arylphosphite, triarylphosphite, arylols, methoxyaryls, diaryl alkylphosphates, diaryl methylphosphite may be minimized or eliminated, so one or more separation steps in which by-products are removed or intermediates are isolated may not be necessary. In certain embodiment, triarylphosphite may be avoided as a by-product. The diaryl alkyphosphonates produced by the present invention may, therefore, be easier to purify or produce at a level of purity sufficient for subsequent reactions.

A wide variety of diaromatic alkylphosphonates may be produced using the present invention, and these may be used as monomers in the synthesis of polymers such as but not limited to polyphosphonates and copolymers of carbonates and phosphonates. These polymers have exceptional fire resistance and are useful in a wide variety of applications encountered in everyday life.

Having generally described the invention, a more complete understanding thereof may be obtained by reference to the following examples that are provided for purposes of illustration only and do not limit the invention.

EXAMPLE 1

$PCl_3$/Phenol/Methanol: 1.0/2.0/1.0

All glassware was oven dried overnight at 110° C. and assembled under a nitrogen purge. A 250 ml 3 neck round bottom flask was equipped with an overhead stirrer, addition funnel, thermometer, water condenser, and nitrogen by-pass. The flask was charged with 28.23 grams (0.30 moles) or phenol and heated, using an oil bath, to 150° C. with stirring. The addition funnel was charged with 13.09 ml (0.15 moles) of phosphorous trichloride, and the phosphorous trichloride was added dropwise to the hot phenol over a 50 minute period. HCl was evolved during the addition. When the addition was complete the temperature was increased to 180° C. and stirred until HCl evolution ceased (about one hour). The reaction mixture was subsequently cooled to 150° C., and 6.08 ml (0.15 moles) or methanol was added over a 10 minute period, HCl evolved during the addition. The mixture was then heated to 180° C. for one hour and, subsequently, cooled to 20° C. 0.6 grams of methyl iodide was then added in one portion, and the mixture was heated to 250° C. for one hour. There was a small exotherm at about 125° C. After stirring at 250° C. for the hour, the reaction mixture was allowed to cool to room temperature.

33.6 grams of crude diphenyl methylphosphonate was produced. Analysis of the product by gas chromatography/mass spectroscopy (GC/MS) showed that 55% of the product was diphenyl methylphosphonate while 35% was phenol believed to be unreacted starting material. Based on this analysis (28.23 g−11.90 g=16.33 g=0.174 mole), 0.174 mole of phenol were consumed in the reaction, and the theoretical yield of on diphenyl methylphosphonate, based on phenol consumption was 21.6 g (0.174 mole=2×248=21.6 g). Therefore, the yield of the reaction based on GC//MS analysis was 18.5 g or 86% of the theoretical yield.

EXAMPLE 2

$PCl_3$/Phenol/Methanol: 1.0/3.5/1.3 (No Additional Catalyst)

Phenol (331 g, 3.525 moles) was placed in a three neck round bottom flask equipped with a mechanical stirrer, a vacuum/gas port and an addition funnel and heated to 65-70° C. under nitrogen. Phosphorous trichloride (137.3 g, 1.0 mole) was added to the heat phenol dropwise via the addition funnel over a three hour period under nitrogen. Following the complete addition of the phosphorous trichloride, the reaction mixture was stirred at 70° C. for an additional hour. The temperature was then increased to 250° C. under nitrogen until all of the excess phenol had distilled off. The reaction mixture was allowed to cool to room temperature under nitrogen. The next day the temperature was raised to 260° C. and methanol was slowly added. During the addition of methanol the temperature varied from 260° C. to 204° C. After the methanol addition was complete, the reaction temperature was maintained between 210° C. to 215° C. and the reaction was stirred. An aliquot was removed and analyzed by gas chromatography (GC) every hour until no trace of triphenylphosphite could be detected. After 1 hour, the GC analysis indicated that 2.031% triphenylphosphite remained in the reaction mixture. After 2 hours, no triphenylphosphite was detected by GC.

The results of the GC analyses on the crude reaction product are presented in the table below. The by-products include anisole (methoxybenzene) and dimethylphenylphosphite (DMPP(i)).

| GC Analyses of Crude Product from Example 2 | | | | | | |
|---|---|---|---|---|---|---|
| | Anisol 9.16* | Phenol 9.9* | DMPP(i) 13.6* | P-diester 17.17* | TPP(i) 19.7* | Total |
| Analysis % | 5.643 | 31.014 | 1.684 | 49.163 | 0.000 | 87.504 |
| Normalized | 6.449 | 35.443 | 1.924 | 56.184 | 0.000 | 100.00 |
| Yield(g) | 23.092 | 126.914 | 6.889 | 201.184 | 0.000 | 358.08 |
| Yield(moles) | 0.214 | 1.350 | 0.037 | 0.811 | 0.000 | |
| Reacted PCl$_3$(mol.) | | | 0.037 | 0.811 | 0.000 | 0.848 |
| Used or recovered Phenol (mol.) Distil = 0.388 | 0.214 | 1.350 | 0.037 | 1.622 | 0.000 | 3.611 |

*= Elution time
DMPP(i) = Dimethylphenylphosphite
TPP(i) = Triphenylphosphite
P-diester = Diphenylmethylphosphonate Based on the quantity of phosphorus trichloride in the crude product, the diphenyl methylphosphonate yield was 95.6% of theoretical.

EXAMPLES 3-15

Additional experiments were performed to determine the effect of varying the ratio of reactants on the product composition and purity. The following examples (3-15) were prepared according to the following general reaction procedure. In a few examples there are slight differences in the reaction conditions as noted in the respective table entry.

Phosphorus trichloride was added dropwise to phenol heated to and maintained at 65-70° C. over a 2 to 3 hour period with stirring. After the addition was complete, this temperature was maintained for an hour with stirring. The temperature was subsequently increased to about 250° C. and excess phenol were distilled off. The reaction was then cooled to room temperature and left under a nitrogen atmosphere for about 12 to 16 hours.

The temperature was subsequently increased to 250° C. and a methanol/methyl iodide solution or, in the examples where no catalyst was used, methanol alone was added to the stirring reaction mixture. The temperature varied from about 250° C. to about 210° C. during this addition. After the addition was complete, the temperature of the reaction mixture was maintained at about 210° C. to about 250° C. for an additional hour with stirring. The reaction mixture was then cooled to room temperature and the crude reaction product was analyzed by GC-MS. The results are presented in the following tables.

| PCl$_3$/Phenol/Methanol: 1.0/3.5/1.1 (Examples 3-6) | | | | |
|---|---|---|---|---|
| | Example 3 | Example 4 | Example 5 | Example 6 |
| Ratio of P-Diester/Catalyst | 200 | 296 | 578 | 1017 |
| Moles of PCl$_3$ Reacted, % | 92 | 95 | 82 | 84 |
| Yield, % (relative to conversion of PCl$_3$ to P-Diester) | 88 | 88% | 87.7 | 85.5 |
| Yield, % [relative to conversion of PCl$_3$ to TPP (i)] | 4.7 | 7.10 | 4.5 | 8.80 |
| Yield, % [relative to conversion of PCl$_3$ to DMPP(i)] | 7.3 | 4.80 | 6.8 | 5.70 |
| Yield, % [relative to conversion of PCl$_3$ to TPP(a)] | 0 | 0 | 0 | 0 |
| Reaction time, 2$^{nd}$ step | 1 h | 1 h | 1 h | 1 h |
| Mole % Catalyst to PCl$_3$ | 0.64 | 0.45 | 0.23 | 0.11 |

For further abbreviations see Example 2
TPP(a) = triphenylphosphate

| PCl$_3$/Phenol/Methanol: 1.0/3.5/1.3 (Examples 7-10) | | | | |
|---|---|---|---|---|
| | Example 7 | Example 8 | Example 9 | Example 10 |
| Ratio of P-Diester/Catalyst | | 1111 | 2222 | infinity |
| Moles of PCl$_3$ Reacted, % | 87 | 84 | 71 | 85 |
| Yield, % (relative to conversion of PCl$_3$ to P-Diester) | 95.7 | 93.6 | 91.7 | 95.6 |
| Yield, % [relative to conversion of PCl$_3$ to TPP (i)] | 0 | 0 | 0 | 0 |
| Yield, % [relative to conversion of PCl$_3$ to DMPP(i)] | 4.3 | 6.5 | 8.3 | 4.4 |
| Yield, % [relative to conversion of PCl$_3$ to TPP(a)] | 0 | 0 | 0 | 0 |
| Reaction time, 2$^{nd}$ step, to get rid of TPP(i) | 1 h | 2 h | 2 h | 2 h |
| Mole % Catalyst to PCl$_3$ | 0.39 | 0.09 | 0.04 | 0 |

For abbreviations see Example 2

| PCl$_3$/Phenol/Methanol: 1.0/3.05-2.5/1.3 (Examples 11, 12) | | |
|---|---|---|
| | Example 11 PCl$_3$/Phenol/ Methanol: 1.0/3.05/1.3 | Example 12 PCl$_3$/Phenol/ Methanol: 1.0/2.5/1.3 |
| Ratio of P-Diester/Catalyst | Infinity | Infinity |
| Moles of PCl$_3$ Reacted, % | 75 | 69 |
| Yield, % (relative to conversion of PCl$_3$ to P-Diester) | 90.8 | 95.5 |
| Yield, % (relative to conversion of PCl$_3$ to TPP (i)) | 0 | 0 |
| Yield, % (relative to conversion of PCl$_3$ to DMPP(i)) | 9.20 | 3.50 |
| Yield, % (relative to conversion of PCl$_3$ to TPP(a)) | 0 | 0 |
| Reaction time, 2$^{nd}$ step, to get rid of TPP(i) | 2 h | 1 h |
| Mole % Catalyst to PCl$_3$ | 0 | 0 |

For abbreviations see Example 2

| PCl₃/Phenol/Methanol: 1.0/2.0 or 3.05/1.3 (Examples 13, 14) | | |
|---|---|---|
| | Example 13 PCl₃/Phenol/Methanol: 1.0/2.0/1.3 | Example 14 PCl₃/Phenol/Methanol: 1.0/3.05/1.3 Rxn temp for 2$^{nd}$ step 200-210° C. |
| Ratio of P-Diester/Catalyst | Infinity | Infinity |
| Moles of PCl₃ Reacted, % | 41 | 75 |
| Yield, % (relative to conversion of PCl₃ to P-Diester) | 79.3 | 86.8 |
| Yield, % (relative to conversion of PCl₃ to TPP (i)) | 0 | 0 |
| Yield, % (relative to conversion of PCl₃ to DMPP(i)) | 4.43 | 13.2 |
| Yield, % (relative to conversion of PCl₃ to TPP(a)) | 16.26 | 0 |
| Reaction time, 2$^{nd}$ step, to get rid of TPP(i) | 1 h | 5 h |
| Mole % Catalyst to PCl₃ | 0 | 0 |

For abbreviations see Example 2

| PCl₃/Phenol/Methanol: 1.0/4.0/1.3 (Example 15) | |
|---|---|
| | Example 15 PCl₃/Phenol/Methanol: 1.0/4.0/1.3 |
| Ratio of P-Diester/Catalyst | Infinity |
| Moles of PCl₃ Reacted, % | 77 |
| Yield, % (relative to conversion of PCl₃ to P-Diester) | 96.10 |
| Yield, % (relative to conversion of PCl₃ to TPP (i)) | 0 |
| Yield, % (relative to conversion of PCl₃ to DMPP(i)) | 3.9 |
| Yield, % (relative to conversion of PCl₃ to TPP(a)) | 0 |
| Reaction time, 2$^{nd}$ step, to get rid of TPP(i) | 2 h |
| Mole % Catalyst to PCl₃ | 0 |

For abbreviations see Example 2

In summary, when the reaction temperature is only from 200° C. to 210° C., somewhat less PCl₃ is converted to product. Consequently, lower yields of the desired product (diaryl alkylphosphonate) and higher quantities of DMPP(i) are obtained. However, if the reaction temperature is from 210° C. to 250° C., higher yields of high purity product and significantly less DMPP(i) are obtained. We have found that reaction temperatures above 250° C. are less desirable because undesirable degradation of the product may occur.

Preferable results were obtained in reactions with PCl₃ to phenol molar ratios of 1.0/2.5-4.0, and PCl₃ to methanol molar ratios of 1.0/1.2-1.3. Acceptable results were obtained with no catalyst or a relatively low concentration of catalyst (0.1 to about 1.0 mole percent relative to 1.0 mole of phosphorus trichloride).

EXAMPLE 16

PCl₃/Phenol/Methanol: 1.0/3.5/1.3 (Methanol Added Under the Surface)

Phenol (330 g, 3.5 moles) was placed in three neck round bottom flask equipped with a mechanical stirrer, a vacuum/gas port and an addition funnel and heated to 65-70° C. under nitrogen. To the heated phenol, phosphorus trichloride (137.3 g, 1.0 mole) was added dropwise via the addition funnel over a three hour period. After the addition was complete, the reaction mixture was stirred at 70° C. for an hour. The addition funnel was removed and replaced with a side arm consisting of a collection flask and a thermometer, and the temperature was increased to 250° C. under nitrogen until all of the excess phenol had distilled off. The reaction mixture was allowed to cool to room temperature under nitrogen. The reaction mixture was then heated to 250° C. and a mixture of methanol (41.65 g, 1.3 moles) and methyl iodide (0.70 g, 0.005 moles) was slowly added underneath the surface of the reaction mixture using an electric micro-pump. Adding the methanol underneath the reaction surface provides for longer contact time with the reaction mixture allowing for the chemical reaction to have more time to occur before the methanol turns to vapor. This approach provides a constant stream of methanol with increased contact time for improved reaction efficiency, conversion time and product yield. It also allows for an increased feed rate of methanol that reduces the reaction time by one-half compared to the dropwise addition method. During this addition process, the reaction temperature was in the range of 210 to 250° C. The crude yield of product was 342.1 g. Analysis of the crude product is provided in the table below.

| Analysis of Crude Product from Example 16 | | | | | | |
|---|---|---|---|---|---|---|
| | Anisole 9.16* | Phenol 9.9* | DMPP(i) 13.6* | P-Diester 17.17* | TPP(i) 19.7* | Total |
| Analysis, % | 4.119 | 28.522 | 2.234 | 51.751 | 0 | 86.72 |
| Normalized | 4.750 | 32.890 | 2.680 | 59.680 | 0 | 100.00 |
| Yield, g | 16.424 | 112.619 | 9.177 | 204.350 | 0 | 342.41 |
| Yield, moles | 0.151 | 1.198 | 0.049 | 0.824 | 0 | |
| PCl₃, moles in | | | 0.049 | 0.824 | 0 | 0.873 |
| Phenol, mole Distilled = 0.540 | 0.151 | 1.198 | 0.049 | 1.648 | 0 | 3.586 |

For abbreviations see Example 2

The reaction resulted in 87.3% PCl$_3$ conversion with a product (diphenyl methylphosphonate) yield of 94.4%.

EXAMPLE 17

PCl$_3$/Methanol: 1.0/3.5/1.3 (Methanol Added Beneath the Surface)

Phenol (330 g, 3.5 moles) was placed in a three neck round bottom flask equipped with a mechanical stirrer, a vacuum/gas port and an addition funnel and heated to 65-70° C. under nitrogen. To the heated phenol, phosphorus trichloride (137.3 g, 1.0 mole) was added dropwise via the addition funnel over a three hour period. After the addition was complete, the reaction mixture was stirred at 70° C. for an hour. The addition funnel was removed and replaced with a side arm consisting of a collection flask and a thermometer, and the temperature was increased to 250° C. under nitrogen until all of the phenol had distilled off. The reaction mixture was allowed to cool to room temperature under nitrogen. The reaction mixture was heated to 250° C. and a mixture of methanol (41.65 g, 1.3 moles) and methyl iodide (0.35 g, 0.0025 moles) was slowly added underneath the surface of the reaction mixture using an electric micro-pump. During this addition process, the reaction temperature was in the range of 210° C. to 250° C. The yield of crude product was 342.1 g. Analysis of the crude product is provided in the table below.

| | Analysis of Crude Product from Example 17 | | | | | |
|---|---|---|---|---|---|---|
| | Anisole 9.16* | Phenol 9.9* | DMPP(i) 13.6* | P-Diester 17.17* | TPP(i) 19.7* | Total |
| Analysis, % | 4.969 | 29.345 | 3.002 | 51.868 | 0 | 89.184 |
| Normalized | 5.570 | 32.895 | 3.365 | 58.144 | 0 | 100.00 |
| Yield, g | 18.521 | 109.379 | 11.189 | 193.335 | 0 | 332.51 |
| Yield, moles | 0.171 | 1.164 | 0.060 | 0.780 | 0 | |
| PCl$_3$, moles in | | | 0.060 | 0.780 | 0 | 0.840 |
| Phenol, mole Distilled = 0.540 | 0.171 | 1.164 | 0.060 | 1.560 | 0 | 3.593 |

For abbreviations see Example 2

The reaction resulted in 84.0% PCl$_3$ conversion with a product (diphenylmethylphosphonate) yield of 92.86% and 7.14% DMPP(i). After 1 additional hour of reaction at 210° C. in 250° C., only 1.518% of TPP(i) remained. After reacting for yet one additional hour, no detectable TPP(i) remained in the crude product.

EXAMPLE 18

Comparative Example: Commercially Pure Triphenylphosphite as Starting Material and Low Catalyst Concentration Triphenylphosphite (310 g, 1.0 moles) was placed in a three neck round bottom flash equipped with a magnetic stirrer, a nitrogen inlet and an addition funnel and heated in an oil bath to 260° C. under nitrogen. A mixture of methanol (41.65%, 1.30 moles) and methyl iodide (0.35 g, 0.0025 moles) was added using a microfeed pump. Initially a slight reflux was observed, but as the methanol concentration increased, refluxing was accompanied by a rapid drop in the reaction temperature to 235° C. At this point the addition was stopped to allow the temperature to return to 250-260° C. However, the temperature did not increase even after halting the methanol addition for over 30 minutes. Addition of methanol/catalyst solution was started again, and the intensity of the reflux increased notably. After the addition was complete, the reaction temperature had dropped to 135° C., and heating for an additional 3 hours did not affect significant change. The reaction was allowed to cool and the crude product was analyzed by GC. The reaction resulted in the following mixture: triphenylphosphite 91.81%; phenol 8.19% and diphenyl methylphosphonate 0%.

Example 18 shows that the desired product is not formed when commercially pure triphenylphosphite is used as the starting material and a low concentration of an alkylation catalyst is employed. In fact, the reaction results in the recovery of starting material indicating that little or no reaction occurred. This is in sharp contrast to the method described above and in Examples 1-17. Even in the examples where no catalyst is used, a high yield of the desired product (diphenylmethylphosphonate) is obtained. Additionally, the product is largely free of phosphorus contaminants.

Although the present invention has been described in considerable detail with reference to certain preferred embodiments thereof, other versions are possible. Therefore the spirit and scope of the appended claims should not be limited to the description and the preferred versions contained within this specification.

What is claimed is:

1. A method for making optionally substituted diaryl alkylphosphonate comprising:

reacting phosphorous trihalide of formula:

PX$_3$, or X$_a$P(Oaryl)$_b$ wherein X is F, Cl, Br or I, a and b are 1 or 2 and a and b combined equals 3 and optionally substituted arylol of general formula (3):

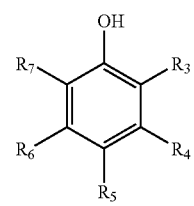

(3)

wherein R$_3$, R$_4$, R$_5$, R$_6$, and R$_7$ are, independently, hydrogen, C$_1$-C$_{20}$ alkyl, aromatic or aryl group, trifluoromethyl, nitro, cyano, halide, $C_1$-$C_{20}$ alkyl ether, benzyl halide, benzyl ether, aromatic or aryl ether, or substituted versions of these to form a first mixture;

adding optionally substituted alkanol of 1 to 20 carbon atoms or more having at least one hydroxyl group substituent to the first mixture to form a second mixture; and heating the mixture to form optionally substituted diaryl alkylphosphonate of general formula (1);

(1)

wherein $R_1$ may be an aromatic or aryl group, or a substituted aryl group of formula (2):

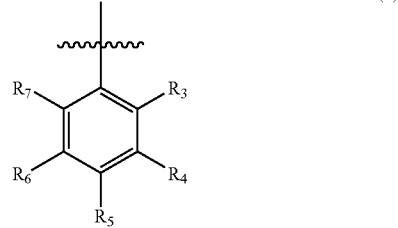
(2)

wherein $R_3$, $R_4$, $R_5$, $R_6$, and $R_7$ may independently be any substituent including but not limited to hydrogen, $C_1$-$C_{20}$ alkyl, aromatic or aryl group, trifluoromethyl, nitro, cyano, halide (F, Cl, Br, I), $C_1$-$C_{20}$ alkyl ether, benzyl halide, benzyl ether, aromatic or aryl ether, or substituted versions of these.

2. The method of claim 1, wherein the phosphorous trihalide is phosphorous trichloride.

3. The method of claim 1, wherein the optionally substituted alkanol is methanol.

4. The method of claim 1, wherein the optionally substituted alkanol is added under a surface of the first mixture.

5. The method of claim 1, wherein the optionally substituted alkanol is added onto a surface of the first mixture.

6. The method of claim 1, wherein the optionally substituted arylol is phenol.

7. The method of claim 1, wherein the second mixture is heated to from about 23° C. to about 260° C.

8. The method of claim 1, wherein the second mixture is heated to from about 200° C. to about 250° C.

9. The method of claim 1, further comprising a step of removing volatile products from the second mixture.

10. The method of claim 1, further comprising the step of removing volatile products from the first mixture.

11. The method of claim 1, wherein the optionally substituted arylol is from about 2 to about 4 molar equivalents of the phosphorous trihalide.

12. The method of claim 1, wherein the optionally substituted alkanol is from about 1 to about 3 molar equivalents of the phosphorous trihalide.

13. The method of claim 1, further comprising a step of adding an alkylating catalyst to the second mixture.

14. The method of claim 13, wherein the alkylating catalyst is selected from alkyl halides, sufonic acid esters, sulfuric acid esters, sulftones, trifluoromethane sulfuric acid, perfluorobutane sulfuric acid, prefluorooctane sulfuric acid, and combinations thereof.

15. The method of claim 13, wherein the alkylating catalyst is methyl iodide.

16. The method of claim 13, wherein the alkylating catalyst is from about 0 to about 5% by weight of the phosphorous trihalide.

17. The method of claim 13, wherein the alkylating catalyst is from about 0 to about 0.4% by weight of the phosphorous trihalide.

18. The method of claim 13, wherein the optionally substituted alkanol is added to a reacted mixture of phosphorous trihalide, an optionally substituted arylol, and an alkylating catalyst under a surface of the first mixture.

19. The method of claim 13, wherein the optionally substituted alkanol is added to a reacted mixture of phosphorous trihalide, optionally substituted arylol, and alkylating catalyst onto a surface of the first mixture.

20. The method of claim 1, wherein the first mixture is reacting when the optionally substituted alkanol is added to the first mixture.

21. The method of claim 1, wherein the first mixture has completely reacted when the optionally substituted alkanol is added to the first mixture.

22. The method of claim 1, wherein a commercially relevant yield of optionally substituted diaryl alkylphosphonate is formed.

23. The method of claim 22, wherein a commercially relevant yield is a yield greater than about 50% optionally substituted diaryl alkylphosphonate.

24. The method of claim 22, wherein a commercially relevant yield is a yield greater than about 60% optionally substituted diaryl alkylphosphonate.

25. The method of claim 22, wherein a commercially relevant yield is a yield greater than about 80% optionally substituted diaryl alkylphosphonate.

* * * * *

UNITED STATES PATENT AND TRADEMARK OFFICE
Certificate

Patent No. 7,569,717 B2                                    Patented: August 4, 2009

On petition requesting issuance of a certificate for correction of inventorship pursuant to 35 U.S.C. 256, it has been found that the above identified patent, through error and without any deceptive intent, improperly sets forth the inventorship.
   Accordingly, it is hereby certified that the correct inventorship of this patent is: Dieter Freitag, Chelmsford, MA (US); and Savvas Hadjikyriacou, Chelmsford, MA (US).

Signed and Sealed this Tenth Day of July 2012.

BRANDON FETTEROLF
*Supervisory Patent Examiner*
Art Unit 1628
Technology Center 1600